(12) United States Patent
James et al.

(10) Patent No.: US 8,538,529 B2
(45) Date of Patent: Sep. 17, 2013

(54) POWER CONVERTER FOR USE WITH IMPLANTABLE THERMOELECTRIC GENERATOR

(75) Inventors: Kristofer J. James, Eagan, MN (US); Blair Erbstoeszer, Kirkland, WA (US); Glenn Morita, Everett, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1899 days.

(21) Appl. No.: 11/681,976

(22) Filed: Mar. 5, 2007

(65) Prior Publication Data

US 2007/0253227 A1    Nov. 1, 2007

Related U.S. Application Data

(60) Provisional application No. 60/745,715, filed on Apr. 26, 2006, provisional application No. 60/745,724, filed on Apr. 26, 2006, provisional application No. 60/745,720, filed on Apr. 26, 2006.

(51) Int. Cl.
*H02M 3/335* (2006.01)
*A61N 1/39* (2006.01)
*A61N 1/00* (2006.01)

(52) U.S. Cl.
USPC .............................................. 607/35; 363/19

(58) Field of Classification Search
USPC .......................................................... 607/35
See application file for complete search history.

(56) References Cited

U.S. PATENT DOCUMENTS

| | | | |
|---|---|---|---|
| 3,563,028 A | 2/1971 | Goranson et al. | |
| 3,835,864 A | 9/1974 | Rasor et al. | |
| 3,900,603 A | 8/1975 | Rittmayer et al. | |
| 3,957,541 A | 5/1976 | Bustard et al. | |
| 3,958,324 A | 5/1976 | Alais et al. | |

(Continued)

FOREIGN PATENT DOCUMENTS

| | | |
|---|---|---|
| DE | 19530382 A1 | 2/1997 |
| EP | 0369670 A2 | 5/1990 |

(Continued)

OTHER PUBLICATIONS

"The Electrical Engineering Handbook", ed. Richard C. Dorf, CRC Press, 1997. p. 25, equation 1.46.*

(Continued)

*Primary Examiner* — Carl H Layno
*Assistant Examiner* — Erin Piateski
(74) *Attorney, Agent, or Firm* — Schwegman Lundberg & Woessner, P.A.

(57) ABSTRACT

Method and apparatus for converting the output of a thermoelectric generator to voltages compatible with implantable medical devices is provided. One apparatus includes an implantable thermoelectric generator. The apparatus includes an input terminal for receiving an input voltage generated by a thermoelectric energy converter and a charging inductor connected in series with the input terminal. The apparatus also includes a switching Field Effect Transistor (FET) connected to the inductor, and a capacitor connected to the FET and the input terminal via a diode. The FET is switched with a frequency and duty cycle such that a voltage level at an output terminal is compatible with an implantable medical device. According to various embodiments, the FET is switched using a closed loop feedback system that controls the frequency and duty cycle based on an observed voltage level at the output terminal. Other aspects and embodiments are provided herein.

20 Claims, 5 Drawing Sheets

(56) References Cited

U.S. PATENT DOCUMENTS

| | | | |
|---|---|---|---|
| 4,014,346 A | | 3/1977 | Brownlee et al. |
| 4,520,039 A | | 5/1985 | Ovshinsky |
| 4,536,967 A | | 8/1985 | Beitzer |
| 4,935,345 A | * | 6/1990 | Guilbeau et al. ............... 435/14 |
| 5,129,033 A | | 7/1992 | Ferrara et al. |
| 5,256,857 A | | 10/1993 | Curhan et al. |
| 5,527,346 A | | 6/1996 | Kroll |
| 5,644,184 A | * | 7/1997 | Kucherov ................... 310/306 |
| 5,835,457 A | | 11/1998 | Nakajima |
| 5,889,735 A | | 3/1999 | Kawata et al. |
| 5,897,330 A | | 4/1999 | Watanabe et al. |
| 6,060,166 A | | 5/2000 | Hoover et al. |
| 6,071,351 A | | 6/2000 | Venkatasubramanian |
| 6,131,581 A | * | 10/2000 | Leysieffer et al. ............ 128/899 |
| 6,300,150 B1 | | 10/2001 | Venkatasubramanian |
| 6,407,477 B1 | * | 6/2002 | King et al. ................... 310/306 |
| 6,470,212 B1 | * | 10/2002 | Weijand et al. ................ 607/35 |
| 6,505,468 B2 | | 1/2003 | Venkatasubramanian |
| 6,582,425 B2 | | 6/2003 | Simpson |
| 6,640,137 B2 | * | 10/2003 | MacDonald ................... 607/35 |
| 6,662,570 B2 | | 12/2003 | Venkatasubramanian |
| 6,722,140 B2 | | 4/2004 | Venkatasubramanian |
| 6,828,908 B2 | | 12/2004 | Clark |
| 6,876,123 B2 | | 4/2005 | Martinovsky et al. |
| 7,002,328 B2 | * | 2/2006 | Kernahan et al. ............. 323/283 |
| 7,127,293 B2 | | 10/2006 | MacDonald |
| 7,164,077 B2 | | 1/2007 | Venkatasubramanian |
| 7,282,798 B2 | | 10/2007 | Venkatasubramanian |
| 8,003,879 B2 | | 8/2011 | Erbstoeszer et al. |
| 8,039,727 B2 | | 10/2011 | Erbstoeszer et al. |
| 2001/0023591 A1 | | 9/2001 | Maeda et al. |
| 2001/0052234 A1 | | 12/2001 | Venkatasubramanian |
| 2001/0055660 A1 | | 12/2001 | Tischler et al. |
| 2002/0028314 A1 | | 3/2002 | Tischler et al. |
| 2002/0122683 A1 | | 9/2002 | Kamei et al. |
| 2002/0174660 A1 | | 11/2002 | Venkatasubramanian |
| 2003/0099279 A1 | | 5/2003 | Venkatasubramanian et al. |
| 2003/0126865 A1 | | 7/2003 | Venkatasubramanian |
| 2003/0131609 A1 | | 7/2003 | Venkatasubramanian |
| 2003/0176900 A1 | | 9/2003 | MacDonald |
| 2003/0183269 A1 | | 10/2003 | Maeda et al. |
| 2003/0184941 A1 | | 10/2003 | Maeda |
| 2003/0192582 A1 | * | 10/2003 | Guevara ........................ 136/205 |
| 2003/0230332 A1 | | 12/2003 | Venkatasubramanian et al. |
| 2004/0093041 A1 | | 5/2004 | MacDonald |
| 2004/0095264 A1 | * | 5/2004 | Thomas ............................ 341/53 |
| 2004/0176859 A1 | * | 9/2004 | Chian et al. ...................... 700/12 |
| 2004/0206479 A1 | | 10/2004 | Kroliczek et al. |
| 2005/0038483 A1 | | 2/2005 | MacDonald |
| 2005/0075694 A1 | * | 4/2005 | Schmeling et al. ............. 607/61 |
| 2005/0162142 A1 | * | 7/2005 | Kernahan et al. ............. 323/283 |
| 2005/0171580 A1 | | 8/2005 | MacDonald |
| 2005/0285684 A1 | | 12/2005 | Burgener et al. |
| 2006/0044846 A1 | * | 3/2006 | Hjort et al. ...................... 363/34 |
| 2006/0086118 A1 | | 4/2006 | Venkatasubramanian et al. |
| 2006/0162761 A1 | | 7/2006 | Tanielian |
| 2006/0266043 A1 | | 11/2006 | Jerome |
| 2007/0023077 A1 | | 2/2007 | Tanielian |
| 2007/0251244 A1 | | 11/2007 | Erbstoeszer et al. |
| 2007/0251565 A1 | | 11/2007 | Erbstoeszer et al. |
| 2007/0291514 A1 | | 12/2007 | Shen et al. |
| 2008/0089818 A1 | | 4/2008 | Ammann et al. |
| 2008/0134757 A1 | | 6/2008 | Chen et al. |
| 2008/0184886 A1 | | 8/2008 | Tufts et al. |

FOREIGN PATENT DOCUMENTS

| | | | |
|---|---|---|---|
| EP | 369670 A2 | * | 5/1990 |
| JP | 01-208876 A | | 8/1989 |
| JP | 2001112796 A | | 4/2001 |
| WO | WO-94/16464 A1 | | 7/1994 |
| WO | WO-2005/074463 A2 | | 8/2005 |
| WO | WO-2007/127831 A2 | | 11/2007 |

OTHER PUBLICATIONS

"U.S. Appl. No. 11/681,985, Examiner Interview Summary mailed Jul. 26, 2010", 4 pgs.

"U.S. Appl. No. 11/681,985, Final Office Action mailed May 27, 2010", 20 pgs.

"U.S. Appl. No. 11/681,985, Non-Final Office Action mailed Aug. 21, 2009", 21 pgs.

"U.S. Appl. No. 11/681,985, Non-Final Office Action mailed Sep. 29, 2010", 17 pgs.

"U.S. Appl. No. 11/681,985, Response filed Feb. 22, 2010 to Non-Final Office Action mailed Nov. 21, 2009", 13 pgs.

"U.S. Appl. No. 11/681,985, Response filed Jul. 27, 2010 to Final Office Action mailed May 27, 2010", 17 pgs.

"U.S. Appl. No. 11/681,995, Examiner Interview Summary mailed Aug. 2, 2010", 3 pgs.

"U.S. Appl. No. 11/681,995, Final Office Action mailed Apr. 29, 2010", 13 pgs.

"U.S. Appl. No. 11/681,995, Non-Final Office Action mailed Aug. 24, 2009", 17 pgs.

"U.S. Appl. No. 11/681,995, Response filed Feb. 22, 2010 to Non Final Office Action mailed Aug. 24, 2009", 13 pgs.

"U.S. Appl. No. 11/681,995, Response filed Jul. 28, 2010 to Final Office Action mailed Apr. 29, 2010", 9 pgs.

"U.S. Appl. No. 11/681,985, Notice of Allowance mailed Apr. 15, 2011", 8 pgs.

"U.S. Appl. No. 11/681,985, Response filed Jan. 26, 2011 to Non Final Office Action mailed Sep. 29, 2010", 13 pgs.

"U.S. Appl. No. 11/681,995, Final Office Action mailed Feb. 17, 2011", 15 pgs.

"U.S. Appl. No. 11/681,995, Non Final Office Action mailed Nov. 24, 2010", 15 pgs.

"U.S. Appl. No. 11/681,995, Response filed Jan. 26, 2011 to Non Final Office Action mailed Nov. 24, 2010", 10 pgs.

"U.S. Appl. No. 11/681,995, Response filed Jun. 9, 2011 to Final Office Action mailed Feb. 17, 2011", 10 pgs.

"International Application No. PCT/US2007/067481, International Search Report mailed Feb. 18, 2008", 4 pgs.

"International Application No. PCT/US2007/067481, Written Opinion mailed Feb. 18, 2008", 10 pgs.

Wanjura, H. J., "Future power supply of cardiac pacemakers", *Medizinal Markt*, 3, (w/English Translation), (1969), 98-100.

"U.S. Appl. No. 11/681,995, Notice of Allowance mailed Jun. 24, 2011", 9 pgs.

* cited by examiner

POWER CONVERTER FOR USE WITH IMPLANTABLE THERMOELECTRIC GENERATOR

CLAIM OF PRIORITY AND RELATED APPLICATIONS

This application claims the benefit under 35 U.S.C. 119(e) of U.S. Provisional Patent Application Ser. No. 60/745,715, filed Apr. 26, 2006, U.S. Provisional Patent Application Ser. No. 60/745,724, filed Apr. 26, 2006, and U.S. Provisional Patent Application Ser. No. 60/745,720, filed Apr. 26, 2006, the entire disclosures of which are hereby incorporated by reference in their entirety. The present application is related to the following commonly assigned U.S. patent applications which are filed even date herewith and incorporated herein by reference in their entirety: "Method and Apparatus for In Vivo Thermoelectric Power System," Ser. No. 11/681,985; "Method and Apparatus for Shunt for In Vivo Thermoelectric Power System," Ser. No. 11/681,995.

TECHNICAL FIELD

This disclosure relates generally to thermoelectric energy converters, and more particularly to a power converter for use with implantable thermoelectric generator.

BACKGROUND

Various implantable medical devices require electrical power for their operation. Examples include cardiac rhythm management devices such as pacemakers and implantable cardioverters/defibrillators, and neurostimulators. These devices traditionally use electrochemical power supplies, or batteries, disposed within the device to supply the required electrical power.

Other power sources can be used to supplement battery power, providing benefits including a reduction in the size of the battery required and an extension of the life of the battery. Thermoelectric generators, which convert body heat to electrical current, are one such supplemental power source. However, the voltage output from most thermoelectric generators is far lower than that necessary for use by the above-mentioned implantable medical devices.

Improved systems for converting the output of a thermoelectric generator to voltages compatible with implantable medical devices are needed.

SUMMARY

The above-mentioned problems and others not expressly discussed herein are addressed by the present subject matter and will be understood by reading and studying this specification.

Disclosed herein, among other things, is an apparatus for use with an implantable thermoelectric generator. The apparatus includes an input terminal for receiving an input voltage generated by a thermoelectric energy converter and a charging inductor connected in series with the input terminal. The apparatus also includes a switching Field Effect Transistor (FET) connected to the inductor, and a capacitor connected to the FET and the input terminal via a diode. According to various embodiments, the FET is switched with a frequency and duty cycle such that a voltage level at an output terminal is compatible with an implantable medical device. The capacitor has a capacitance of 1 µF, according to an embodiment. Additional embodiments have other capacitances. Capacitances which are greater than 1 µF are additionally contemplated, including embodiments having 2 µF. The charging inductor includes 22 turns of 34 gauge wire, according to an embodiment. In various embodiments, the apparatus provides power efficiency from the input terminal to the xoutput terminal of 20 to 30%. The FET is switched with a frequency of 10 kHz, according to one embodiment. Additional embodiments have other frequencies. Frequencies which are greater than 1 µF are additionally contemplated, including embodiments having 2 µF. According to various embodiments, the FET is switched using a closed loop feedback system that controls the frequency and duty cycle based on an observed voltage level at the output terminal. The specific values provided herein are not intended to be limiting, but rather serve to provide examples of the range of values contemplated by the present subject matter.

One aspect of this disclosure relates to a method for making a power converter for use with an implantable thermoelectric generator. According to an embodiment, the method includes forming an input terminal for receiving an input voltage generated by a thermoelectric energy converter. The method also includes forming a charging inductor connected in series with the input terminal. The method further includes forming a switching FET connected to the inductor. In addition, the method includes forming a capacitor connected to the FET and the input terminal via a diode. According to various embodiments, the FET is switched with a frequency and duty cycle such that a voltage level at the output terminal is compatible with an implantable medical device.

One aspect of this disclosure relates to a method for converting power from an implantable thermoelectric generator. According to an embodiment, the method includes receiving an input voltage level generated by a thermoelectric energy converter. The method also includes switching a field effect transistor at a frequency to provide oscillating current to an inductor connected in series with the thermoelectric energy converter. The method further includes charging a capacitor using the inductor, converter and transistor to an output voltage level greater than the input voltage level. According to various embodiments, the method also includes providing an output terminal across the capacitor with the output voltage level compatible with an implantable medical device.

This Summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Thermoelectric devices convert thermal gradients to energy, and visa versa. These devices include an interface between dissimilar materials. In some cases the dissimilar materials are metals. In some instances the dissimilar materials are semiconductors. Additional materials which demonstrate the Seebeck effect fall within the present scope.

Despite the availability of materials which demonstrate the Seebeck effect, some applications have yet to benefit from thermoelectric technology. Problems include an inability for some applications to use available thermal gradients. Additionally, some existing designs are too large for practical implantation.

Various embodiments within the scope of the present subject matter provide a thermoelectric energy conversion system for a self-powered device. Self-powered devices contemplated by the present subject matter include implantable devices. Implantable devices contemplated by the present subject matter include, but are not limited to, cardiac rhythm management devices, neurostimulation devices, and other devices not expressly listed herein. In various embodiments, the thermoelectric energy conversion system of the present subject matter operates inside an implantable device, using a thermal gradient present at the implantable device. The embodiments provide enough energy to power electronics within the device.

Figure 1A:
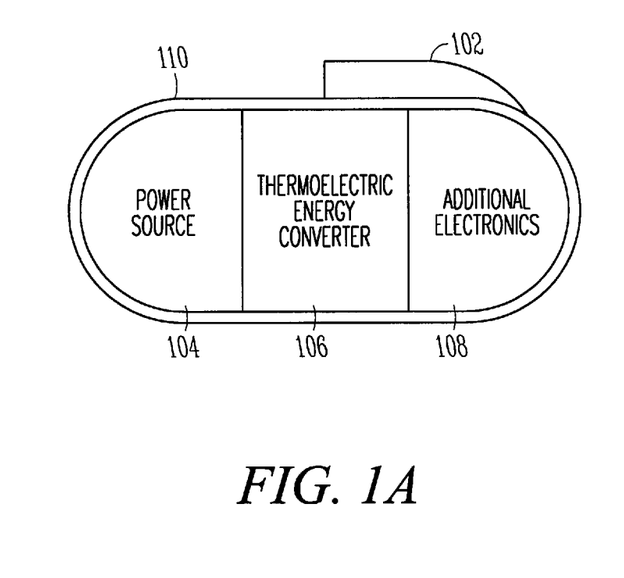
FIG. 1A shows a self-powered device, according to one embodiment of the present subject matter.

FIG. 1A shows a self-powered device, according to one embodiment of the present subject matter. In various embodiments, the self-powered device is suited for use as an implantable medical device. In some of these embodiments, the self-powered device is a cardiac rhythm management device. In additional embodiments, the device is a neurostimulation device. These are only some of the self-powered devices contemplated by the present subject matter. The present subject matter extends to additional devices not expressly listed herein. This front view shows a header 102, and a housing 110. In various embodiments, the housing 110 includes titanium. In additional embodiments, the housing 110 includes stainless steel. Other materials for the housing 110 which are compatible with implanting electronics can optionally be used.

Within housing 110, in some embodiments of the present subject matter, is a power source 104. Power source 104 includes a primary battery, in various embodiments. Some embodiments use one or more lithium ion batteries. Of these, some embodiments use one or more lithium manganese dioxide batteries. Other known primary battery compositions are also be used, in various embodiments. Additionally, power source 104, in various embodiments, includes a secondary battery. Secondary batteries within the present subject matter include rechargeable lithium ion types. Other known secondary batteries are also used. Also, in some embodiments, power source 104 includes a capacitor. Aluminum electrolytic capacitors are used in some embodiments of the present subject matter. Other capacitor compositions additionally fall within the present scope.

Power source 104, in various embodiments, could include a combination of two or more of a primary battery, a secondary battery, or a capacitor. Power source 104, in various embodiments, provides a power source which is available for use in concert with thermoelectric energy converter 106. In various embodiments, power source 104 is used in applications where a power source is needed which delivers power at a rate different from a thermoelectric energy converter. In various embodiments, power source 104 is used for powering electronics when a thermal gradient is not available. Embodiments not including power source 104 additionally fall within the present scope.

The present subject matter provides a thermoelectric energy converter 106 inside of housing 110. In various embodiments, housing 110 includes a first housing portion which is thermally conductive and which has a first housing opening. Housing 110 additionally includes, in various embodiments, a second housing portion which is thermally conductive and which has a second housing opening. In various embodiments, the second housing opening is hermetically sealed to the first housing opening. In various embodiments, the first housing portion and the second housing portion at least partially define an interior volume. Thermoelectric energy converter 106, in various embodiments, is disposed in the interior volume.

Thermoelectric energy converter has a hot pole and a cold pole. In various embodiments, the hot pole is thermally connected to the first housing portion. In additional embodiments, the cold pole is thermally connected to the second housing portion. Configured as such, the self-powered device demonstrated in the present embodiment includes within its housing a thermoelectric energy converter, including the hot pole and the cold pole of the thermoelectric energy converter.

Such a configuration is useful to power additional electronics 108, in various embodiments. In some embodiments, cardiac rhythm management electronics are disposed in the interior volume of housing 110. In some embodiments, neurostimulation electronics are disposed in the interior volume of housing 110. Other electronics variants not expressly listed herein are additionally contemplated by the present subject matter. In some embodiments, the electronics include cardioverter defibrillator electronics. In some embodiments, the additional electronics 108 are powered solely by the thermoelectric energy converter 106, and an additional power source 104 is not included in the device.

In some embodiments, the thermoelectric energy converter 106 is adapted to power pacemaker electronics. In some of these embodiments, power source 104 is included in the device, but does not power pacemaker electronics. For example, power source 104 can provide power for a defibrillation capacitor. In some embodiments using a thermoelectric energy converter 106 to power pacemaker electronics, power source 104 is not included.

In some embodiments, the additional electronics 108 are powered by both the thermoelectric energy converter 106 and the power source 104. In various embodiments, the choice of what power source to use to power additional electronics 108 depends on the energy rate which should to be available. For example, in some embodiments, the thermoelectric energy converter produces power at a rate too low to deliver energy for a defibrillation pulse. In some of these embodiments, power source 104 includes a capacitor used to provide a defibrillation pulse to a patient.

In some embodiments having a power source 104 including a capacitor, multiple capacitor pulses are needed to treat a patient. In these situations, some capacitors are not big enough to hold charge suitable for delivery of multiple pulses. Such housings require an additional power source which can discharge at a high rate to charge the capacitor between defibrillation pulses. In various embodiments, the thermoelectric energy converter 106 cannot discharge at a high enough rate to charge a capacitor in between defibrillation pulses. In such embodiments, additional power source 104 includes additional components, such as a battery, to charge the capacitor at a rate higher than is available from the thermoelectric energy converter 106. In some embodiments, a primary battery is used. Additional embodiments use a secondary battery. Some embodiments use a combination of a primary battery and a secondary battery.

The present subject matter enables a smaller battery to be used to charge a capacitor, in various embodiments. Over the course of the service life of the self-powered device, a battery/capacitor combination may be called upon to deliver therapies multiple times, over multiple episodes. For example, a device may deliver 2 pulses during an episode, and may encounter one episode per year, for 5 years. Batteries in defibrillators are known to last between 3 and 7 years. To provide energy for multiple episodes, a battery should be sized to operate sufficiently during multiple episodes. However, if the battery need only be sized to function appropriately during one episode, it may be smaller. Battery discharge during the episode can be replenished using the thermoelectric device, in various embodiments of the present subject matter.

To provide useful power, the thermoelectric energy converter 106 should be able to harvest thermal energy from the human body and convert it into usable power. Various embodiments of the present subject matter are configured to provide power when a thermal gradient exists which is between approximately 0.5 degrees Celsius, and approximately 5.0 degrees Celsius. Some embodiments provide power using a thermal gradient of approximately 4.3 degrees Celsius. In some of embodiments, the thermoelectric energy converter is adapted to produce power when exposed to a thermal gradient of approximately 0.5 degrees Celsius to approximately 1.5 degrees Celsius. Various embodiments of the present subject matter are configured such that the thermoelectric energy converter is adapted to produce from about 5 microwatts when exposed to a thermal gradient of approximately 0.5 degrees Celsius, to about 80 microwatts when exposed to a thermal gradient of approximately 4.3 degrees Celsius. In some examples, the thermoelectric energy converter is adapted to produce approximately 30 microwatts when exposed to a thermal gradient of approximately 1.0 degrees Celsius. These power production examples are evinced in some of the configurations contemplated by the present subject matter, but are not intended to be limiting of the range of configurations contemplated by the present subject matter. Additionally, the thermal gradients provided herein, and their relationship to power production, are those of example embodiments which are illustrative of the present subject matter, but not demonstrative of the entire range of configurations contemplated by the present subject matter.

Various types of thermoelectric energy converters are used within the present subject matter. In some embodiments, the thermoelectric energy converter includes thermopiles. In some embodiments, the thermoelectric energy converter is a thin film thermoelectric energy converter. Some thermoelectric energy converters include a superlattice. Some thermoelectric energy converters operate using thermotunneling. Other known thermoelectric designs which meet packaging and power requirements of implantable self-powered devices additionally fall within the present scope.

Figure 1B:
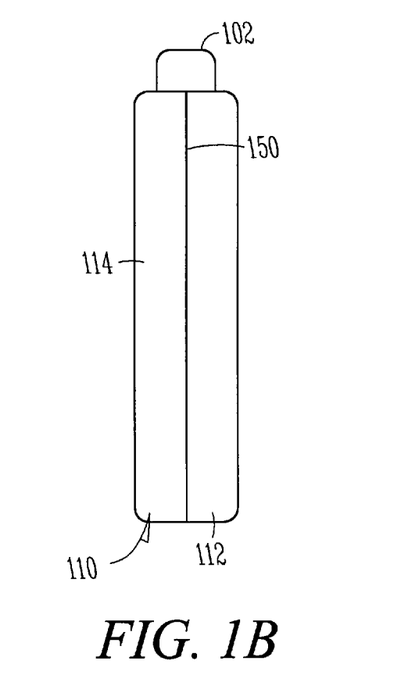
FIG. 1B shows a side view of the self-powered device of FIG. 1A.

FIG. 1B shows a side view of the self-powered device of FIG. 1A. Pictured in the view are header 102 and housing 110. The housing 110 is comprised, in various embodiments, of a first portion 112 and a second portion 114. In various embodiments, first portion 112 is cup shaped and includes a first aperture conformed to a second aperture of the second portion 114, wherein the first and second apertures are hermetically sealed at seam 150.

Figure 2:
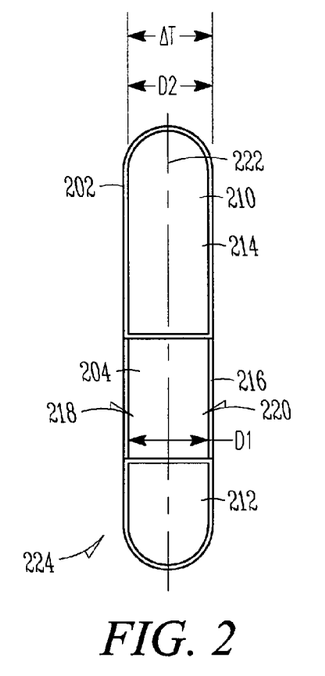
FIG. 2 shows a cross section of a self-powered device, according to one embodiment of the present subject matter.

FIG. 2 shows a cross section of a self-powered device 224, according to one embodiment of the present subject matter. Various embodiments of the present subject matter include a housing. In various embodiments, the housing includes a first housing portion 202 and a second housing portion 214. Various embodiments additionally include electronics 210, an additional power source 212, and a thermoelectric energy converter system 204.

In some embodiments, the first housing portion 202 is cup shaped and the second housing portion 214 is cup shaped. In some examples, the first housing portion and the second housing portion meet, with respective openings conforming to one another along plane 222. Although the first housing portion 202 and the second housing portion 214 of the present subject matter demonstrate such a configuration, other configurations are possible, including ones in which first housing portion 202 and second housing portion 214 conform to one another along an irregular interface. In various embodiments, the first housing portion 202 and the second housing portion 214 are mechanically connected. Some embodiments are welded together. In some embodiments, a laser weld joins the first housing portion 202 and the second housing portion 214.

In various embodiments of the present subject matter, the thermoelectric energy converter system 204 is thermally connected to the first housing portion 202 and the second housing portion 210. For example, some embodiments position a hot pole 218 of a thermoelectric energy converter system 204 adjacent a first housing portion 202, such that the hot pole and the first housing portion are in thermal conduction. In additional embodiments, the cold pole 220 of the thermoelectric energy converter system 204 is positioned adjacent the second housing portion 214, such that the cold pole 220 and the second housing portion 214 are in thermal conduction.

In various embodiments, performance of the thermoelectric energy conversion system 204 is enhanced due to reduced thermal conduction between first housing portion 202 and second housing portion 214. Some embodiments of the present subject matter utilize materials for the first housing portion 202 and/or the second housing portion 214 which are less thermally conductive. Some embodiments, for example, use housing portions constructed of titanium. Titanium has a thermal conductivity of approximately 17 Watts per meter Kelvin, in various embodiments. Additional embodiments use housing portions constructed of stainless steel. Some embodiments of the present subject matter use 3161 stainless steel. Some embodiments of the present subject matter use a stainless steel having a thermal conductivity of approximately 16 watts per meter Kelvin. Other materials for the first and/or second housing portions fall within the present scope.

In some embodiments, the performance of the thermoelectric energy conversion system 204 is enhanced by an interconnection between the first and second housing portions and their respective connections to the hot and cold pole of the thermoelectric energy conversion system. For example, connection 216, in various embodiments, enhances thermal conductivity between second housing portion 214 and cold pole 220 using a thermally conductive grease. Other mediums which enhance thermal conductivity are additionally contemplated, including, but not limited to, epoxy and other adhesives. In some examples, a thermally conductive grease has a thermal conductivity of from about 4 Watts per meter Kelvin to about 5 Watts per meter Kelvin. Additional embodiments weld cold pole 220 to second housing portion 214. Some embodiments include a thermally conductive filler material which thermally interconnects the second housing portion 214 and the cold pole 220. These configurations for connecting the cold pole 220 and the second housing portion 214 apply to connections to the first housing portion 202 and the hot pole 218, in various embodiments.

In various embodiments, the thermoelectric energy converter system 204 has a thickness of D1. In some embodiments, the thermoelectric energy converter is less than the thickness of the thermoelectric energy converter system. Some embodiments include a thermoelectric energy converter system 204 which is less than the thickness D2 of the device 224 in which it is housed. In some embodiments, the thickness D1 is less than 0.020 inches thick. Some embodiments are between 0.020 inches and 0.040 inches thick. Embodiments of the present subject matter are between 0.040 inches and 0.100 inches thick. Embodiments having a thickness D1 which is greater than 0.100 inches thick are also contemplated. These combinations are provided for illustration and are not intended to be limiting as the present subject matter contemplates thicknesses which are not listed herein expressly.

In some embodiments, the connected first housing portion and second housing portion have a substantially plate shaped exterior. In some embodiments, the plate shaped exterior has a first planar surface and a second planar surface, wherein the thermoelectric energy converter system 204 is plate shaped and is disposed in the housing such that a thickness of the thermoelectric energy converter extends away from one of the first planar surface and the second planar surface.

In various embodiments, the device 224 is exposed to a thermal gradient $\Delta T$. In various embodiments, the thermal gradient $\Delta T$ is from about 0.5 degrees Celsius to about 4.3 degrees Celsius. In additional embodiments, the thermal gradient $\Delta T$ is from about 0.5 degrees Celsius to about 1.5 degrees Celsius. In some embodiments, the thermal gradient $\Delta T$ is about 1.0 degrees Celsius. For example, in one embodiment, the hot pole is at 37.0 degrees Celsius, and the cold pole is at 35.5 degrees Celsius.

Transposing this thermal gradient $\Delta T$ to the thermoelectric energy converter system 204 with a small decrease in thermal gradient $\Delta T$ is desirable. As such, in some embodiments, a thermally insulative insert is disposed between first housing portion 202 and second housing portion 214. In some embodiments, the thermally insulative insert is epoxy. In some embodiments, the thermally insulative insert is conformed to first portion 202 and second portion 214 and is hermetically sealed to those portions.

Various methods for assembly fall within the present subject matter. Various embodiments include connecting a thermoelectric energy converter to a device housing, such that a hot pole of the thermoelectric energy converter is connected to a first housing portion, and a cold pole of the thermoelectric energy converter is connected to a second housing portion, with the connected first and second housing portions defining an interior volume in which the thermoelectric energy converter is disposed. Additionally, various embodiments include disposing a converter inside an interior volume defined by a first housing portion and a second housing portion, such that of the thermoelectric energy converter are respectively connected to the first housing portion and the second housing portion.

Some embodiments include packaging, in the interior volume, a defibrillation capacitor powered by a battery. In some embodiments, the battery is a primary battery. In additional embodiments, the battery is a secondary battery.

Various embodiments include connecting the thermoelectric energy converter to cardiac rhythm management electronics disposed in the interior volume. For example, some embodiments include connecting pacemaker electronics disposed in the interior volume to the thermoelectric energy converter, such that the pacemaker electronics are powered by the thermoelectric energy converter. Some embodiments include connecting the thermoelectric energy converter to neurostimulation electronics disposed in the interior volume.

In various embodiments, therapy electronics (such as cardiac rhythm management electronics, neurostimulation electronics, etc.) and a secondary battery are connected to the thermoelectric energy converter. In some of these embodiments, the secondary battery powers the therapy electronics. In some embodiments, the thermoelectric energy converter powers the therapy electronics. In some embodiments, the thermoelectric energy converter powers the secondary battery exclusively. Some embodiments include powering a capacitor with the secondary battery. Capacitors contemplated by the present subject matter include capacitors used as the primary power source for providing shocks for defibrillation.

Some embodiments of the present subject matter include methods of implanting a device having a thermoelectric energy converter of the present subject matter in a patient such that the first housing portion is positioned subcutaneously. Embodiments of the present subject matter additionally include positioning a housing submuscularly. The present subject matter includes additional embodiments, however, which position the device in other areas of the body.

Figure 3:
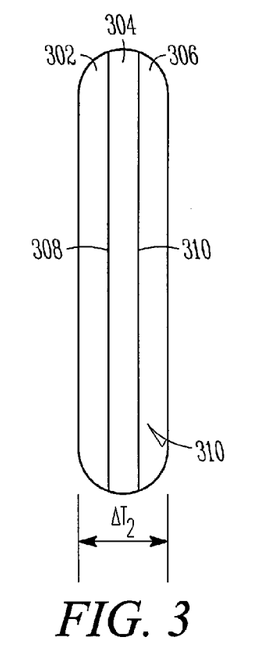
FIG. 3 shows a side view of a self-powered device, according to one embodiment of the present subject matter.

FIG. 3 shows a side view of a self-powered device, according to one embodiment of the present subject matter. In various embodiments, a housing 310 includes a first portion 302, a second portion 306, and an insert 304. Transposing thermal gradient $\Delta T_2$ to the thermoelectric energy converter system decrease in thermal gradient $\Delta T_2$ is desirable. As such, in some embodiments, insert 304 is disposed between first housing portion 302 and second housing portion 306.

In various embodiments, insert 304 is of a lower thermal conductivity than the first portion 302. In additional embodiments, the insert 304 is of a lower thermal conductivity than the second portion 306. In some embodiments, insert 304 includes a thermally insulative material. Some embodiments include a cured resin. In some embodiments, the thermally insulative insert 304 is epoxy. Various additional embodiments include other materials. In some embodiments, the thermally insulative insert is conformed to first portion 302 and second portion 306 and is hermetically sealed to those portions.

Some embodiments do not include an insert, and instead rely on a first portion of a housing and a second portion of a housing each having a low thermal conductivity. For example, some embodiments include a first portion of a housing and a second portion of a housing, with the two portions assembled to one another and defining an interior space. Within the interior space, a thermoelectric energy conversion system extends between the first and second housing portions, in various embodiments. The first and second housing portions include a low conductivity material, in various embodiments. But because, in various embodiments, the first and second energy housings are thin, having a thickness of approximately 0.012 inches, heat passes through them, traveling to the thermoelectric energy conversion system. These embodiments create a thermal gradient which is sufficient to power a thermoelectric energy conversion device.

Various methods for assembly fall within the present subject matter. Various embodiments include connecting a thermoelectric energy converter to a device housing, such that a hot pole of the thermoelectric energy converter is connected to a first housing portion, and a cold pole of the thermoelectric energy converter is connected to a second housing portion, with the connected first and second housing portions defining an interior volume in which the thermoelectric energy converter is disposed. Additionally, various embodiments include disposing a converter inside an interior volume defined by a first housing portion and a second housing portion, such that of the thermoelectric energy converter are respectively connected to the first housing portion and the second housing portion.

Some embodiments include packaging, in the interior volume, a defibrillation capacitor powered by a battery. In some embodiments, the battery is a primary battery. In additional embodiments, the battery is a secondary battery.

Various embodiments include connecting the thermoelectric energy converter to cardiac rhythm management electronics disposed in the interior volume. For example, some embodiments include connecting pacemaker electronics disposed in the interior volume to the thermoelectric energy converter, such that the pacemaker electronics are powered by the thermoelectric energy converter.

In various embodiments, cardiac rhythm management electronics and a secondary battery are connected to the thermoelectric energy converter. In some of these embodiments, the secondary battery powers the cardiac rhythm management electronics. In some embodiments, the thermoelectric energy converter powers the cardiac rhythm management electronics. In some embodiments, the thermoelectric energy converter charges the secondary battery exclusively. Also, some embodiments include powering a defibrillation capacitor with the secondary battery.

Figure 4:
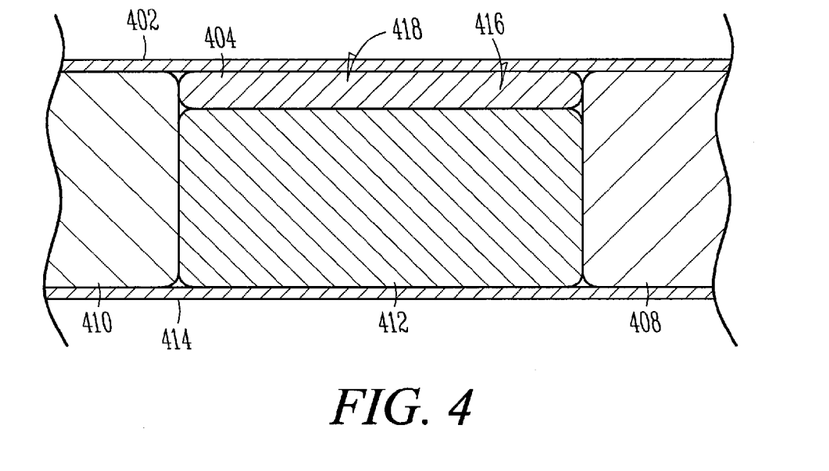
FIG. 4 illustrates a schematic diagram of an apparatus for converting power from a thermoelectric energy converter, according to one embodiment of the present subject matter.

FIG. 4 is a partial cross section of a self-powered implantable device having a thermal shunt, according to one embodiment of the present subject matter. Various embodiments of the present subject matter include a first housing portion 414 which is thermally conductive and which has a first case opening. Various embodiments include a second housing portion 402 which is thermally conductive and which has a second case opening, with the material defining the second case opening being hermetically sealed to the material defining the first case opening, and with the first housing portion and the second housing portion at least partially defining an interior volume. The present subject matter includes additional electronics 408 disposed in the interior volume, in various embodiments. In some embodiments, the additional electronics include cardiac rhythm management electronics.

Various embodiments additionally include a thermal shunt 412 disposed in the interior volume. The thermal shunt 412 is constructed such that heat at first housing portion 414 is conducted to the thermoelectric energy converter. As such, in various embodiments, the thermal shunt is constructed from a material having a high thermal conductivity. Materials contemplated by the present subject matter include, but are not limited to, copper, aluminum, silver, other materials and alloys thereof. Another possible material is a carbon fiber composite having a structure which is anisotropic and which demonstrates a high level of thermal conductivity. An anisotropic material is beneficial as it reduces the amount of energy conducted to an additional power source 410 and additional electronics 408. In various embodiments, the anisotropic material includes carbon fiber strands held in an orientation by a cured resin. In some of these embodiments, epoxy is the cured resin. Diamond powder is an additional material which is suitable for construction of a shunt, according to various embodiments of the present subject matter. Other materials which are thermally conductive additionally fall within the present scope. One embodiment uses a shunt which is a heat pipe.

Thermal shunt 412 is interconnected to other components in a variety of ways. In some examples, the shunt is interconnected to the first housing portion 414 using a weld. In additional examples, the shunt is interconnected to the first housing portion 414 with a thermal grease having a high thermal conductivity. In some embodiments, an adhesive interconnects thermal shunt 412 to other components. Additional mediums are also contemplated, including but not limited to, epoxy and additional adhesives.

Also, various embodiments include a thermoelectric energy converter 404 disposed in the interior volume and adjacent the thermal shunt, the thermoelectric energy converter having a first pole 416 and a second pole 418, with the first pole thermally connected to the first housing portion, and the second pole thermally connected to the shunt. In various embodiments, the first pole 416 is a hot pole. In various embodiments, the second pole 418 is a cold pole. The thermoelectric energy converter 404, in various embodiments, is film shaped. In some embodiments, the thermoelectric energy converter 404 is a thin film device.

Figure 5:
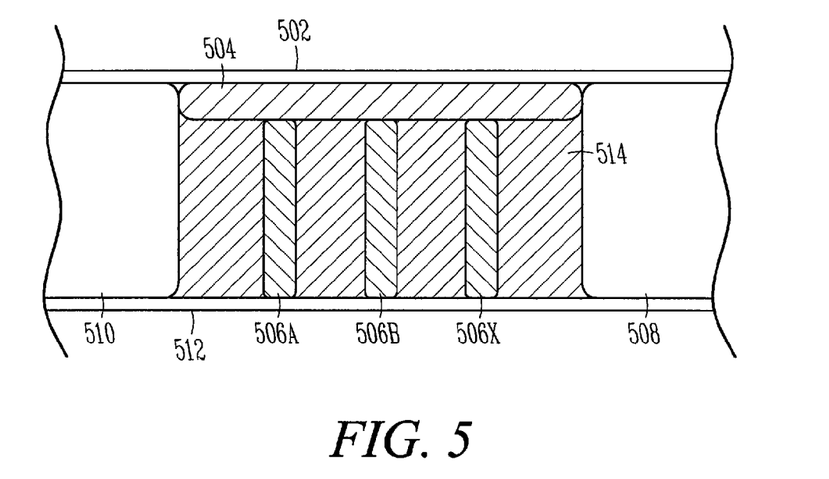
FIG. 5 shows a partial cross section side view of a self-powered device, according to one embodiment of the present subject matter.

FIG. 5 shows a partial cross section side view of a self-powered device, according to one embodiment of the present subject matter. Various embodiments of the present subject matter include a thermoelectric energy converter 504 which is in adjacent a thermal shunt having multiple beams 506A, 506B, ..., 506x. In various embodiments, the multiple beams 506A, 506B, ..., 506X are configured for passage through various components 514 of a self-powered device. In some embodiments, the multiple beams 506A, 506B, ..., 506X pass through an additional power source. In some of these embodiments, the multiple beams 506A, 506B, ..., 506X pass through a battery. In some of these embodiments, the multiple beams 506A, 506B, ..., 506X pass through a capacitor. In additional embodiments, the multiple beams 506A, 506B, ..., 506X pass through electronics.

In various embodiments, the multiple beams 506A, 506B, ..., 506X are tubular columns of a conductive material. Materials contemplated by the present subject matter include, but are not limited to, copper, aluminum, silver, other materials and alloys thereof. Other embodiments use additional shapes for the beams. Additional embodiments include alternate materials such as an anisotropic composite.

The illustration additionally shows a first case portion 502, a second case portion 512, an additional power source 510, and additional electronics 508. The inclusion of the additional power source 510 as illustrated is not limiting, as some embodiments of the present subject matter integrate all additional power sources into additional components 514. Also, the inclusion of the additional electronics 508 as illustrated is not limiting, as some embodiments of the present subject matter integrate all additional electronics into additional components 514.

Figure 6:
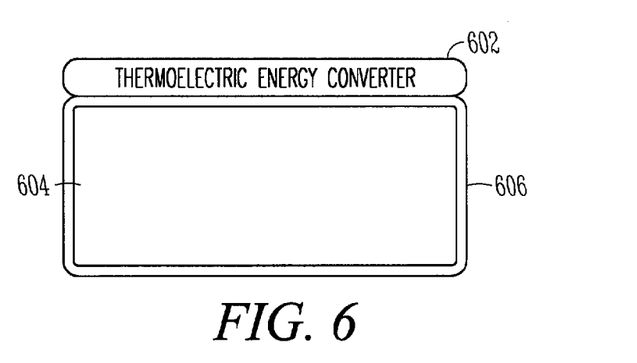
FIG. 6 shows a cross section of a thermoelectric energy converter and additional components disposed in a shunt, according to one embodiment of the present subject matter.

FIG. 6 shows a cross section of a thermoelectric energy converter and additional components disposed in a shunt, according to one embodiment of the present subject matter. The illustration shows thermoelectric energy converter 602, shunt 606, and additional components 604. In various embodiments, additional components 604 include a battery. In some embodiments, additional components 604 include a capacitor. Various embodiments dispose electronics in shunt 606. Electronics include one or more of pacemaker control circuits, cardioverter defibrillator circuits, and other circuits. A combination of components listed herein additionally are disposed in shunt 606, in various embodiments. Components not listed herein, or combinations of components not listed herein, may additionally be disposed in shunt 606. Some embodiments include a solid shunt 606 having no components disposed within. Some embodiments include a hollow shunt 606 having no components disposed within.

In accordance with the requirements of components disposed in shunt 606, shunt 606 includes feedthrough provisions, in various embodiments. For example, in some battery embodiments, battery electrodes are disposed in shunt 606. In some of these embodiments, the anode of the battery is connected to a feedthrough, and the cathode is connected to the shunt. In additional embodiments, the cathode is connected to a feedthrough, and the anode is connected to the shunt 606. Some embodiments include a feedthrough for the battery anode and the capacitor cathode.

Additionally, in some capacitor embodiments, capacitor electrodes are disposed in shunt 606. In some of these embodiments, the anode of the capacitor is connected to a feedthrough, and the cathode is connected to the shunt. In additional embodiments, the cathode is connected to a feedthrough, and the anode is connected to the shunt 606. Some embodiments include a feedthrough for the capacitor anode and the capacitor cathode.

It is important to note that in some embodiments, an electrolyte is in contact with the interior of the shunt 606, and functions as part of the components housed in the shunt 606. For example, in some embodiments, a capacitor using the shunt 606 as a housing includes a thermally conductive electrolyte which further benefits the heat conducting properties of the shunt 606.

Figure 7:
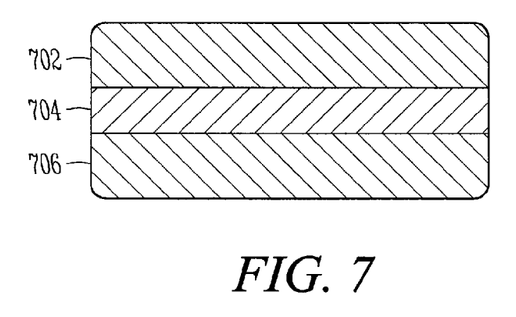
FIG. 7 shows a cross section of a shunt and a thermoelectric energy converter, according to one embodiment of the present subject matter.

FIG. 7 shows a cross section of a shunt and a thermoelectric energy converter, according to one embodiment of the present subject matter. In various embodiments, a thermoelectric energy converter 704 is disposed between a first shunt 702 and a second shunt 706. The first shunt 702 and the second shunt 706 are respectively adjacent first and second portions of a self-powered device housing, in various embodiments. First shunt 702 and second shunt 706 are solid in some embodiments. Additional embodiments include one or both of the first shunt 702 and the second 706 in a hollow configuration.

Figure 8:
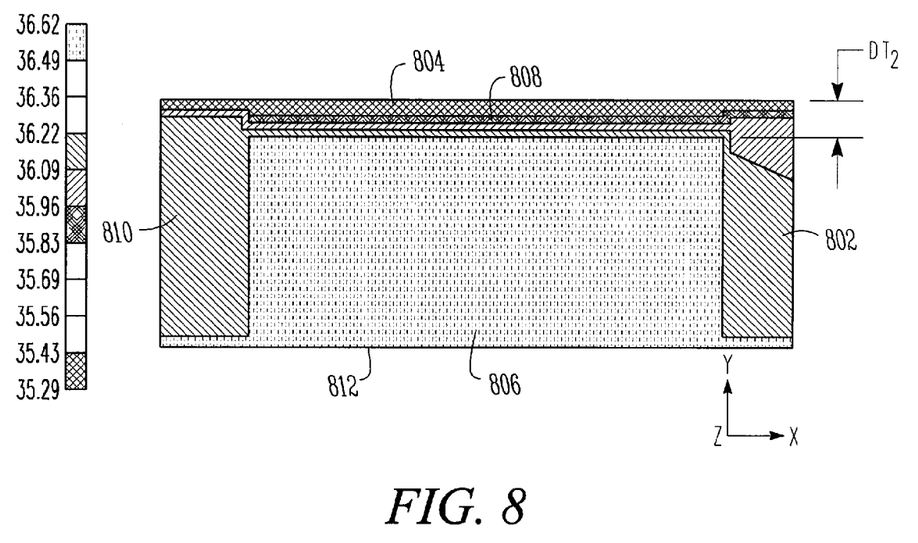
FIG. 8 is cross section or a self-powered device showing thermal gradients, according to one embodiment of the present subject matter.

FIG. 8 is cross section or a self-powered device showing thermal gradients, according to one embodiment of the present subject matter. The illustration shows a thermal representation of the temperature at a first housing portion 804, a thermoelectric device 808, a shunt 806, a second housing portion 812, an additional power source 810, and additional electronics 802. Pictured is temperature gradient $\Delta T_2$, which in the illustrated example represents a temperature drop of approximately 0.9 degrees Celsius across the thermoelectric energy converter. Such a temperature gradient is sufficient to provide power of around forty microwatts to one or both of the additional electronics 802 and the additional power source 810. Other temperature gradients $\Delta T_2$ and power outputs fall within the present scope. Applications which could produce $\Delta T_2$ include implantation below a patient's skin, with the first case portion 804 positioned subcutaneously. Embodiments of the present subject matter additionally include positioning a housing submuscularly. These power production examples are evinced in some of the configurations contemplated by the present subject matter, but are not intended to be limiting of the range of configurations contemplated by the present subject matter. Additionally, the thermal gradients provided herein, and their relationship to power production, are those of example embodiments which are illustrative of the present subject matter, but not demonstrative of the entire range of configurations contemplated by the present subject matter.

Thermoelectric generators convert heat to electrical power. This electrical power typically has current in the milliampere (mA) range and voltage in the microvolt (μV) range. The voltage required by a typical implantable medical device is several orders of magnitude larger. Additionally, excess energy can be stored for future use, but most energy storage systems require voltages higher than what is generated by a thermoelectric generator. The present subject matter provides an apparatus and method for converting the output of a thermoelectric generator to voltages compatible with an implantable medical device.

Figure 9:
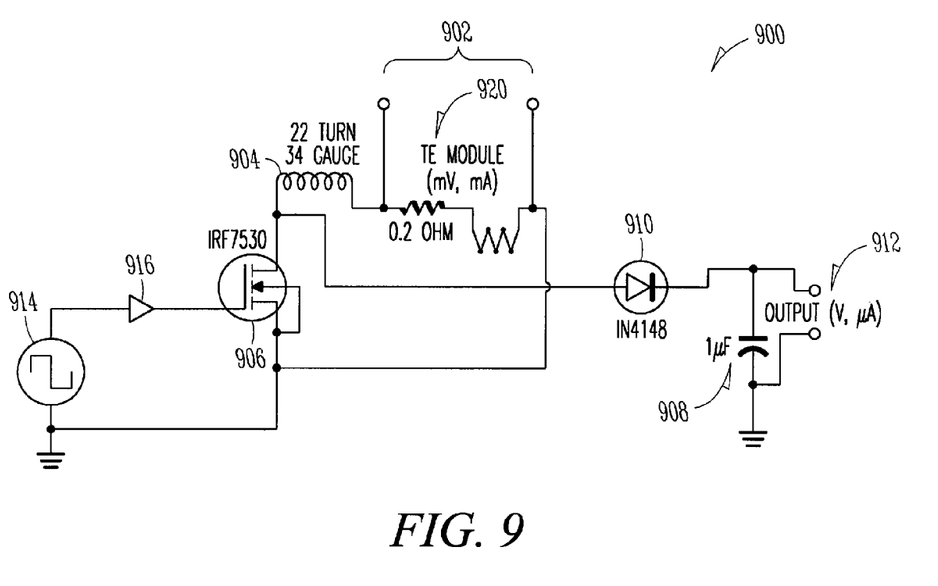
FIG. 9 illustrates a schematic diagram of an apparatus for converting power from a thermoelectric energy converter, according to one embodiment of the present subject matter.

FIG. 9 shows a circuit for converting power from a thermoelectric energy converter, according to one embodiment of the present subject matter. To provide power in a form compatible with various loads, an energy conversion circuit is provided. In various embodiments, the electronics of the present subject matter are adapted to control the conduction of energy between the thermoelectric energy converter and a power source. In some embodiments, these electronics control the transmission of energy to a secondary battery. In additional embodiments, the electronics control the transmission of energy between a battery and a defibrillation capacitor. In some embodiments, the thermoelectric energy converter powers a defibrillation capacitor concurrent with a battery.

FIG. 9 illustrates a schematic diagram of an apparatus for converting power from a thermoelectric energy converter, according to one embodiment of the present subject matter. The apparatus 900 includes an input terminal 902 for receiving an input voltage generated by a thermoelectric energy converter 920 and a charging inductor 904 connected in series with the input terminal. The apparatus also includes a switching Field Effect Transistor (FET, 906) connected to the inductor. A capacitor 908 is connected to the FET and the input terminal via a diode 910. According to various embodiments, the FET 906 is switched with a frequency and duty cycle such that a voltage level at the output terminal 912 is compatible with an implantable medical device. Implantable medical devices refer to devices used for in situ sensing and/or therapy delivery. Examples include, but are not limited to, chronically implanted devices such as pacemakers, cardioverters/ defibrillators, and neurostimulators.

The capacitor 908 has a capacitance of 1 μF, according to an embodiment. According to various embodiments, the charging inductor 904 includes a hand-wrapped wire inductor. The charging inductor 904 includes 22 turns of 34 gauge wire, according to an embodiment. Other types and sizes of inductors are within the scope of this disclosure. In various embodiments, the apparatus provides power efficiency from the input terminal 902 to the output terminal 912 of 20 to 30%. The FET 906 is switched with a frequency of 10 kHz, according to one embodiment. According to various embodiments, the FET 906 is switched using a closed loop feedback system that controls the frequency and duty cycle based on an observed voltage level at the output terminal 912. The FET is switched with a duty cycle of at least 90%, according to various embodiments.

The apparatus functions as an inductive boost circuit. The depicted implementation minimizes the number of circuit elements, and further reduces the need for customized circuit elements. The circuit elements are appropriate for inclusion on an application-specific integrated circuit (ASIC). The low part count allows for easy implementation and minimizes package size. The resistance of the inductor and FET are minimized to increase efficiency of the converter circuit.

The switching FET is selected to have a low resistance when switched "on". According to an embodiment, the FET has an "on" resistance of approximately 40 ohms. The inductor is selected to have a low resistance as well, to improve the efficiency of the apparatus. The apparatus takes as an input the relatively low voltage from the thermoelectric generator (8-100 μV, according to various embodiments) and builds the voltage on the capacitor. The voltage level on the capacitor, or output voltage, is determined by the loading of the output circuit, the heat flux across the thermoelectric generator, the efficiency of the thermoelectric generator, and the pulse frequency and duty cycle of the switching FET. The frequency and duty cycle can by controlled using a closed loop system. According to an embodiment, the frequency and duty cycle are controlled using logic. The frequency and duty cycle are controlled using pulse-width modulation, according to an embodiment. An oscillating supply 914 connected to the gate of the FET 906 via logic 916 can be used to set and adjust frequency and duty cycle. In an embodiment, the oscillating supply is controlled using feedback from an observed output voltage.

The FET 906 includes circuit element model IRF7530, for example, in an embodiment. The diode 910 includes circuit element model 1N4148, for example, in an embodiment. Other circuit elements having the similar characteristics can be used without departing from the scope of the disclosure.

Some embodiments of the present subject matter include methods of implanting a device having a thermoelectric energy converter of the present subject matter in a patient such that the first housing portion is positioned subcutaneously. Embodiments of the present subject matter additionally include positioning a housing submuscularly. Some of these embodiments position the housing of between the pectoral muscle and the skin. The present subject matter includes additional embodiments, however, which position the device in other areas of the body.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and other embodiments will be apparent to those of skill in the art upon reviewing the above description. The scope of the present subject matter should be determined with reference to the appended claims, along with the full scope of equivalents to which such claims are entitled.

What is claimed is:

1. An apparatus, comprising:
    a metallic an implantable housing defining an interior volume;
    a thermoelectric energy converter disposed in the interior volume;
    a power conversion circuit disposed in the interior volume including an input terminal coupled to an output terminal of the thermoelectric energy converter to receive power from the thermoelectric energy converter, the power conversion circuit comprising:
        a charging inductor connected in series with the input terminal;
        a switching FET connected to the inductor; and
        a capacitor connected to the FET and the input terminal via a diode, the capacitor adapted to accumulate charge;
    a power source disposed in the interior volume and coupled to the power conversion circuit to receive power from the power conversion circuit; and
    therapy electronics disposed in the interior volume and coupled to the power source to convert power from the power source into electronic pulse therapy,
    wherein the FET is adapted to switch at a frequency and duty cycle such that the power conversion circuit inputs a voltage level to the power source, and wherein the power source is adapted to power the therapy electronics.

2. The apparatus of claim 1, wherein the capacitor has capacitance of 1 μF.

3. The apparatus of claim 1, wherein an input voltage generated by the thermoelectric energy converter is at most 100 μV.

4. The apparatus of claim 1, wherein power efficiency from the input terminal to the output terminal is at least 20%.

5. The apparatus of claim 1, wherein power efficiency from the input terminal to the output terminal is 30%.

6. The apparatus of claim 1, wherein the FET is switched with a frequency of 10 kHz.

7. The apparatus of claim 1, wherein the FET is switched with a duty cycle of at least 90%.

8. The apparatus of claim 1, wherein the FET is switched using a closed loop feedback system.

9. The apparatus of claim 8, wherein the closed loop feedback system controls the frequency and duty cycle based on an observed voltage level at the output terminal.

10. The apparatus of claim 9, wherein the frequency and duty cycle are controlled using pulse-width modulation.

11. The apparatus of claim 1, wherein the charging inductor includes a hand-wrapped wire inductor.

12. The apparatus of claim 1, wherein the charging inductor has 22 turns.

13. The apparatus of claim 1, wherein the charging inductor includes 34 gauge wire.

14. An apparatus, comprising:
    an implantable housing that includes a first portion that is metallic and thermally conductive, and a second portion that is metallic and thermally conductive, the first portion and the second portion joined and hermetically sealed together defining an interior volume, with the first portion in direct thermal conduction with the second portion; and
    electronics disposed in the interior volume, the electronics including thermoelectric energy converter electronics disposed in the interior volume, the thermoelectric energy converter electronics including a hot pole and a cold pole, with the hot pole thermally conductive to the first portion of the housing and the cold pole thermally conductive to the second portion of the housing, a power conversion circuit disposed in the interior volume including an input terminal coupled to an output terminal of the thermoelectric energy converter to receive power from the thermoelectric energy converter, the power conversion circuit comprising:
- a charging inductor connected in series with an input terminal;
- a switching FET connected to the inductor; and
- a capacitor connected to the FET and the input terminal via a diode, the capacitor adapted to accumulate charge;

a power source disposed in the interior volume and coupled to the power conversion circuit to receive power from the power conversion circuit; and therapy electronics disposed in the interior volume and coupled to the power source to convert power from the power source into electronic pulse therapy, wherein the FET is adapted to switch at a frequency and duty cycle such that the power conversion circuit inputs a voltage level to the power source, wherein the power source is adapted to power the therapy electronics, and wherein the thermoelectric energy converter electronics are adapted to convert a temperature differential between the first portion of the housing and the second portion of the housing to provide power for at least part of the apparatus.

15. The apparatus of claim 14, wherein the thermoelectric energy converter electronics include a thermopile.

16. The apparatus of claim 14, wherein the hermetically sealed housing includes titanium.

17. The apparatus of claim 14, wherein the hermetically sealed housing includes stainless steel.

18. The apparatus of claim 14, further comprising a thermally conductive grease disposed between the hot pole and the first portion of the housing.

19. The apparatus of claim 14, wherein the thermoelectric energy converter electronics include a thin film thermoelectric energy converter.

20. The apparatus of claim 19, wherein the thermoelectric energy converter electronics are less than approximately 0.100 inches thick.

* * * * *